United States Patent [19]

Yoshihara et al.

[11] Patent Number: 5,164,306
[45] Date of Patent: Nov. 17, 1992

[54] PROCESS FOR PRODUCING 5'-INOSINIC ACID BY FERMENTATION

[75] Inventors: Yasuhiko Yoshihara; Yoshio Kawahara; Yasutsugu Yamada; Sigeho Ikeda, all of Kawasaki, Japan

[73] Assignee: Ajinomoto Co., Inc., Tokyo, Japan

[21] Appl. No.: 472,415

[22] Filed: Jan. 31, 1990

Related U.S. Application Data

[63] Continuation of Ser. No. 6,161, Jan. 23, 1987, abandoned.

[51] Int. Cl.$^5$ ............................................. C12P 19/32
[52] U.S. Cl. ........................................ 435/92; 435/88; 435/244
[58] Field of Search .................. 435/92, 95, 106, 114, 435/115, 116, 112, 244, 822, 830, 839, 840, 843, 849, 874, 252.1

[56] References Cited

FOREIGN PATENT DOCUMENTS 62-61593 9/1985 Japan .

OTHER PUBLICATIONS

Grant et al., Chemical Dictionary, 1987, pp. 82, 133–134, 265 and 518.
Lukin et al., Biological Abstracts, vol. 67, 1979, #56673.
Yoshihara et al., Chemical Abstracts, vol. 107(19), 1987, #174368u.

Primary Examiner—Johnnie R. Brown
Assistant Examiner—Pamela S. Webber
Attorney, Agent, or Firm—Oblon, Spivak, McClelland, Maier & Neustadt

[57] ABSTRACT

A process for producing 5'-inosinic acid by culturing 5'-inosinic acid-producing bacteria in a medium containing inosine, and cane molasses, sucrose or glucose as the main carbon source and containing at least one of L-methylglycine, N,N-dimethylglycine, N,N,N-trimethylglycine and (2-hydroxyethyl)trimethylammonium in an amount effective to enhance the yield of 5'-inosinic acid, and harvesting the 5'-inosinic acid produced.

6 Claims, No Drawings

PROCESS FOR PRODUCING 5'-INOSINIC ACID BY FERMENTATION

This application is a Continuation of application Ser. No. 006,151, filed on Jan. 23, 1987, now abandoned.

DETAILED DESCRIPTION OF THE INVENTION

1. Field of Industrial Application

The present invention relates to L-amino acids such as L-glutamic acid, L-lysine, L-glutamine, L-arginine, L-phenylalanine, L-threonine, L-isoleucine, L-histidine, L-valine, L-serine, L-ornithine, L-citrulline, L-tyrosine, L-tryptophane and L-leucine, etc. and 5'-inosinic acid which have been widely utilized for seasonings, feed additives, medicines, etc.

2. Prior Art

L-Amino acids such as L-glutamic acid, L-lysine, L-glutamine, L-arginine, L-phenylalanine, L-threonine, L-isoleucine, L-histidine, L-valine, L-serine, L-ornithine, L-citrulline, L-tyrosine, L-tryptophane and L-leucine, etc. and 5'-inosinic acid have hitherto been produced by fermentation using microorganisms belonging to the genus Brevibacterium, the genus Corynebacterium, the genus Bacillus or the genus Escherichia, etc. in an industrial scale.

3. Problem to be solved by the invention

A problem to be solved by the present invention is to develop a process for producing L-amino acids or 5'-inosinic acid by fermentation at low costs in an industrial scale.

Means for solving the problem

As a result of extensive investigations with an attempt to improve the yield of L-amino acids as described above or 5'-inosinic acid by fermentation process, the present inventors have found that by fermentation of media supplemented with a definite amount of at least one substance selected from the group consisting of N-methylglycine (hereafter simply referred to as MG), N,N-dimethylglycine (hereafter simply referred to as DMG), N,N,N-trimethylglycine (hereafter simply referred to as TMG) and [2-hydroxyethyl]-trimethyl ammonium (hereafter simply referred to as HETMA), the yield of the desired L-amino acids or nucleic acid can be markedly improved. In order to develop a method for industrially producing L-amino acids or 5'-inosinic acid at lower costs, the present invention has been achieved based on the finding described above. Namely, the present invention relates to a process for producing an L-amino acid or 5'-inosinic acid which comprises culturing L-amino acid-producing bacteria or 5'-inosinic acid-producing bacteria in a medium containing at least one substance selected from the group consisting of MG, DMG, TMG and HETMA to produce an L-amino acid or 5'-inosinic acid and harvesting the L-amino acid or 5'-inosinic acid.

The finding that the incorporation of MG, DMG, TMG and HETMA in media containing sugars and other main carbon sources could improve the yield of L-amino acids or 5'-inosinic acid by fermentation process over a wide range is unknown. The fermentation of L-serine from L-betaine using the genus Pseudomonas or the genus Escherichia (Published Unexamined Japanese Patent Application No. 49-134896) and fermentation of L-amino acids using choline as a main carbon source, using the genus Pseudomonas, is merely known. However, in L-serine fermentation from betaine, betaine is specified as a precursor of serine, from which any improved yield cannot be readily expected over a wide range of L-amino acid fermentation. Further, in the L-amino acid fermentation using choline as a main carbon source, choline is used as only one main carbon source and the yield of L-amino acid is merely trace.

On the other hand, it is known that the addition of Stephen's waste by-produced at steps during manufacturing of beet sugar to media, in a definite amount can markedly improve the yield of L-amino acids or 5'-inosinic acid by fermentation (Published Unexamined Japanese Patent Application No. 59-216593). However, any finding that even in media supplemented with Stephen's waste, the yield of L-amino acids or 5'-inosinic acid by fermentation process could be markedly improved by further adding MG, DMG, TMG or HETMA thereto is unknown. The present invention is based on the novel finding that enables great increase in the yield of L-amino acids or 5'-inosinic acid by fermentation process, which is extremely useful from an industrial aspect.

The L-amino acid, as used in the present invention, refers to L-amino acids such as L-glutamic acid, L-lysine, L-glutamine, L-arginine, L-phenylalanine, L-threonine, L-isoleucine, L-histidine, L-valine, L-serine, L-ornithine, L-citrulline, L-tyrosine, L-tryptophane and L-leucine, etc. and even though they are L-amino acids other than described herein, the process of the present invention is applicable as far as they are produced by fermentation.

The L-amino acid-producing bacteria as used in the present invention can be any microorganism as far as they are capable of producing the aforesaid L-amino acids.

Specifically there can be used:

1. L-Glutamic acid-producing bacteria *Brevibacterium divaricatum* ATCC 14020 *Brevibacterium flavum* ATCC 14067 *Brevibacterium lactofermentum* ATCC 13869 *Brevibacterium lactofermentum* FERM-P 5012 (AJ 11360) *Corynebacterium acetoacidophilum* ATCC 13870 *Corynebacterium glutamicum* ATCC 13032

2. L-Lysine-producing bacteria *Brevibacterium flavum* FERM-P 1708 (AJ 3419) *corynebacterium glutamicum* FERM-P 1709 (AJ 3420) *Brevibacterium lactofermentum* FERM-P 1712 (AJ 3425) *Brevibacterium lactofermentum* FERM-P 1711 (AJ 3424) *Brevibacterium flavum* ATCC 21475 *Corynebacterium glutamicum* ATCC 12416 *Brevibacterium lactofermentum* ATCC 11470 *Corynebacterium acetoglutamicum* ATCC 11472 (AJ 11094)

3. L-Glutamine-producing bacteria *Brevibacterium flavum* FERM-P 4272 *Corynebacterium acetoacidophilum* ATCC 13870 *Microbacterium flavum* FERM-BP 664 (AJ 3684) *Brevibacterium flavum* FERM-BP 662 (AJ 3409) *Corynebacterium acetogluamicum* ATCC 13870 *Corynebacterium glutamicum* FERM-BP 663 (AJ 3682)

4. L-Arginine-producing bacteria *Brevibacterium flavum* FERM-P 4948 *Corynebacterium glutamicum* FERM-P 7274 (AJ 12093) *Brevibacterium flavum* NRRL 12235 (AJ 11337) *Corynebacterium acetoglutamicum* NRRL 12239 (AJ 11342)

5. L-Phenylalanine-producing bacteria *Brevibacterium lactofermentum* FERM-P 6517 *Brevibacterium Flavum* FERM-P 1916 (AJ 3439) *Corynebacterium flutamicum* ATCC 21670 *Arthrobacter citreus* ATCC 21422 *Brevibacterium lactofermentum* ATCC 21420 *Corynebacterium acetoacidophilum* ATCC 21421

*Brevibacterium flavum* NRRL 12269 (AJ 11476) *Corynebacterium glutamicum* ATCC 21670

6. L-Threonine-producing bacteria *Escherichia coli* FERM-P 4900 (AJ 11334) *Corynebacterium glutamicum* FERM-P 5835 (AJ 11654) *Brevibacterium flavum* FERM-P 4164 (AJ 11172) *Brevibacterium lactofermentum* FERM-P 4180 (AJ 11178) *Brevibacterium flavum* ATCC 21269 *Corynebacterium acetoacidophilum* ATCC 21270

7. L-Isoleucine-producing bacteria *Brevibacterium flavum* FERM-P 3672 *Brevibacterium lactofermentum* FERM-P 4192 (AJ 11190) *Corynebacterium glutamicum* FERM-P 756 (AJ 12150) *Corynebacterium glutamicum* FERM-P 757 (AJ 12151) *Corynebacterium glutamicum* FERM-P 758 (AJ 12153) *Brevibacterium flavum* FERM-BP 759 (AJ 12149) *Brevibacterium flavum* FERM-BP 760 (AJ 12152)

8. L-Histidine-producing bacteria *Brevibacterium flavum* FERM-P 2317 *Brevibacterium lactofermentum* FERM-P 1565 (AJ 3386) *Corynebacterium glutamicum* ATCC 14297 *Brevibacterium lactofermentum* ATCC 21086 *Corynebacterium acetoacidophilum* ATCC 21407 *Brevibacterium flavum* ATCC 21406 (AJ 3225) *Bacillus subtilis* FERM-BP 217 (AJ 11733) *Arthrobacter citreus* ATCC 21412

9. L-Valine-producing bacteria *Brevibacterium lactofermentum* FERM-P 1845 *Brevibacterium flavum* FERM-P 512 (AJ 3276) *Corynebacterium lactofermentum* FERM-P 1968 (AJ 3455) *Escherichia coli* NRRL 12285 (AJ 11470)

10. L-Serine-producing bacteria *Corynebacterium glycinophilum* FERM-P1687 *Brevibacterium lactofermentum* FERM-P 1371 (AJ 3360) *Pseudomonas megarubessens* FERM-P 4532 (AJ 11262)

11. L-Ornithine-producing bacteria *Brevibacterium lactofermentum* FERM-P 5936 (AJ 11678) *Corynebacterium glutamicum* FERM-P 5644 (AJ 11589) *Arthrobacter citreus* ATCC 21040 *Corynebacterium glutamicum* ATCC 13232

12. L-Citrulline-producing bacteria *corynebacterium glutamicum* FERM-P 5643 (AJ 11588) *Brevibacterium flavum* FERM-P 1645 (AJ 3408)

13. L-Tyrosine-producing bacteria *Corynebacterium glutamicum* FERM-P 5836 (AJ 11655) *Brevibacterium flavum* FERM-P 7914 (AJ 12180) *Bacillus subtilis* FERM-P 6758 (AJ 11968)

14. L-Tryptophane-producing bacteria *Bacillus subtilis* FERM-P 5286 (AJ 11483) *Brevibacterium lactofermentum* FERM-P 7127 (AJ 12044) *Brevibacterium flavum* FERM-P 2551 *Corynebacterium glutamicum* FERM-P 7128 (AJ 12052) *Brevibacterium flavum* ATCC 21427 *Brevibacterium flavum* FERM-BP 114 (AJ 11667) *Bacillus subtilis* FERM-BP 208 (AJ 11713) *Brevibacterium flavum* FERM-BP 475 (AJ 12022) *Corynebacterium glutamicum* FERM-BP 478 (AJ 12118) *Bacillus subtilis* FERM-BP 200 (AJ 11709)

15. L-Leucine-producing bacteria *Brevibacterium lactofermentum* FERM-P 1769 (AJ 3427) *Brevibacterium flavum* FERM-P 420 (AJ 3226) *Corynebacterium glutamicum* FERM0P 1966 (AJ 3453) *Brevibacterium flavum* FERM-BP 755 (AJ 3686) *Corynebacterium glutamicum* FERM-BP 756 (AJ 12150) *Corynebacterium glutamicum* FERM-BP 757 (AJ 12151) *Brevibacterium flavum* FERM-BP 759 (AJ 12149)

16. 5'-Inosinic acid-producing bacteria *Corynebacterium SP* FERM-P 4973 (AJ 11352) *Corynebacterium equi* FERM-P 4969 (AJ 11347) *Corynebacterium equi* FERM-P 4971 (AJ 11350) *Corynebacterium equi* FERM-P 5397 (AJ 11552) *Corynebacterium equi* FERM-P 6261 (AJ 11749) *Corynebacterium equi* FERM-P 6255 (AJ 11743) *Brevibacterium ammoniagenes* FERM-P 7949 (AJ 12192) *Bacillus subtilis* FERM-P 4120 (AJ 11158) *Bacillus subtilis* FERM-P 6441 (AJ 11820), etc.

As the basic media for producing L-amino acids or 5'-inosinic acid which can be used in the present invention, conventionally known media for producing L-amino acids suited for L-amino acid-producing bacteria and media suited for fermentation of 5'-inosinic acid can be used.

In more detail, as main carbon sources, there can be used sugars such as glucose, sucrose, fructose, maltose, sweet potato molassess, sweet potato blackstrap molasses, beet molasses, beet blackstrap molasses, crude sugar, saccharified starch liquid, saccharified cellulose liquid, saccharified pulp liquid, lactose, etc.; fatty acids such as acetic acid, propionic acid, benzoic acid, etc.; organic acids such as pyruvic acid, citric acid, succinic acid, fumaric acid, malic acid, etc.; alcohols such as ethyl alcohol, butyl alcohol, etc.; singly or as admixture thereof. In addition, precursors of the desired L-amino acids in the biosynthetic path and the like can also be used.

As nitrogen sources, there can be used ammonium salts such as ammonium sulfate, ammonium chloride, ammonium nitrate, ammonium acetate, etc.; urea, liquid ammonia, ammonia water, further amino acid mixtures which are organic nitrogen compounds, corn steep liquor, Casamino acid, yeast extract, soybean hydrolysate, peptone, meat extract etc. As inorganic salts there can be used phosphates, magnesium salts, calcium salts, potassium salts, sodium salts, iron salts, manganese salts, zinc salts, copper salts and other trace metals, if necessary. Further, if necessary, there can also be used vitamins such as biotin, thiamine, etc.

Conditions for culture in the present invention are the same as in ordinary amino acid fermentation. While the conditions are somewhat varied depending upon L-amino acids or strain used, the culture temperature is preferably 20 to 40° C., particularly 28° to 37° C. With respect to pH, good results are obtained when the pH is controlled to be neutral. Culture is carried out under aerial conditions such as aerial, agitation, shake culture, etc. A period for culture is generally 1 to 7 days but the period can also be acid from each amino acid fermentation solution, treatment with ion exchange resin and other known methods for recovery can be used.

MG ($CH_3NHCH_2COOH$), DMG (($CH_3)_2NCH_2COOH$), TMG (($CH_3)_3N^+$ $CH_2COO^-$ or $(OH)^-(CH_3)_3N^+CH_2COOH$) and HETMA (($OH)^-(CH_3)_3N^+CH_2$ $CH_2COOH$) and salts thereof are accessible not only as reagents but also as industrial products at low costs in large quantities. MG is known as sarcosine and naturally occurring in flower moss; MG is synthetically prepared by condensation of methylamine and chloroacetic acid or Strecker's synthesis of amino acid, etc. DMG is obtained by reacting dimethylamine . TMG is k.nown as glycine betaine and contained in sugar beet, cotton seed, etc. in large quantities and, synthesized by reaction of chloroacetic acid with trimethylamine. HETMA is known as choline, contained in radish leaf, etc. in large quantities and synthesized by reacting trimethylamine with a concentrated aqueous solution of ethylene oxide. Further various salts of them are commercially available; for example, sodium salt of MG, hydrochlorides of DMG and TMG, and chloride, hydrogentartarate, dihydrogencitrate, gluconate, etc. of HETMA are industrially produced and easily available.

MG, DMG, TMG or HETMA which are used in the present invention may be in the form of salts thereof or may be substituted with naturally occurring materials containing them.

To use MG, DMG, TMG or HETMA in the present invention, they may be incorporated, singly or in combination of two or more, in fermentation medium in a concentration of 0.01 to preferably in a concentration of 0.05 to 2.0%. To incorporate them in fermentation medium, they may be previously added to fermentation medium followed by incubation; alternatively, they may be incorporated at once, in several portions or continuously during incubation. Further they may be added to seed culture which is then incorporated in main fermentation.

EXAMPLE 1

A seed medium containing 3 g/dl of glucose, 0.1 g/dl of $KH_2PO_4$, 0.05 g/dl of $MgSO_4.7H_2O$, 1 mg/dl of $FeSO_4.7H_2O$, 1 mg/dl of $MnSO_4.4H_2O$, 0.5 g/dl of urea, 30 μg/l of biotin, 100 μg/l of thiamine hydrochloride and soybean protein hydrolysate containing 50 mg/dl as the total nitrogen, was adjusted pH to 7.5 and 50 ml of the seed medium was charged in a 500 ml flask having a shoulder followed by sterilization with heating. *Brevibacterium lactofermentum* ATCC 13869 was inoculated on the medium and shake cultured for 16 hours while keeping at 31.5° C.

On the other hand, as a medium for producing glutamic acid, a medium containing 8.0 g/dl of cane molasses (as sugar), 0.2 g/dl of $KH_2PO_4$, 0.1 g/dl of $MgSO_4.7H_2O$, 2.0 mg/dl of $FeSO_4.4H_2O$, 200 μg/l of thiamine hydrochloride, 30 mg/dl of soybean protein hydrolysate (as the total nitrogen) and 200 mg/dl of Stephen's concentrated waste (2.0 g/dl of total nitrogen concentration) as the total nitrogen concentration and a medium further containing 0.01 to 5 g/dl of TMG, were prepared. After adjusting the pH to 7.8, 285 ml each was charged in a 1.0 liter small sized fermenter followed by sterilization with heating at 115° C. for 10 minutes.

On each medium was inoculated 15 ml each of the seed culture solution obtained by previous incubation and, aerial agitation culture was carried out at 31.5° C. During the culture period, the pH of the culture solution was maintained at 7.8 with ammonia gas and at the same time, previously sterilized cane molasses was supplemented to control the sugar in the culture solution to 2–4 g/dl calculated as sucrose, whereby culture was carried out. At an appropriate time during the culture, polyoxyethylene sorbitan monopalmitate was supplemented. At the time when a rate of the sugar was discontinued and the fermentation was completed in 28 to 40 hours. The amount of L-glutamic acid accumulated in each culture solution was measured and the yield based on the sugar was determined. The results are shown in Table 1.

TABLE 1

| Addition Amount of TMG | Amount of L-Glutamic Acid (g/dl) | Yield Based on Sugar (%) |
|---|---|---|
| 0 | 10.0 | 52.0 |
| 0.01 | 10.3 | 52.5 |
| 0.05 | 10.5 | 53.1 |
| 0.25 | 10.7 | 53.6 |
| 0.5 | 10.7 | 54.7 |

TABLE 1-continued

| Addition Amount of TMG | Amount of L-Glutamic Acid (g/dl) | Yield Based on Sugar (%) |
|---|---|---|
| 1.0 | 10.8 | 55.5 |
| 2.0 | 10.5 | 53.8 |
| 3.0 | 10.5 | 52.5 |
| 5.0 | 9.8 | 51.5 |

EXAMPLE 2

A seed medium containing 5 g/dl of glucose, 0.2 g/dl of $(NH_4)_2SO_4$, 0.2 g/dl of urea, 0./15 g/dl of $KH_2PO_4$, 0.04 g/dl of $MgSO_4.7H_2$), 1 mg/dl of $FeSO_4.7H_2O$, 100 μg/l of thiamine hydrochloride, 3 μg/l of biotin and 30 mg/dl of soybean portein acid hydrolysate as the total nitrogen, was adjusted pH to 7.0 and 50 ml of the seed medium was charged in a 500 flask having a shoulder followed by sterilization with heating. Glutamine fermentation bacteria or *Brevibacterium flavum* FERM-BP 662 was inoculated on the medium and shake cultured for 12 hours while keeping at 31.5° C.

On the other hand, 285 ml of a medium containing 13 g/dl of glucose, 0.25 g/dl of $KH_2PO_4$, 40 mg/dl of $MgSO_4.7H_2O$, 1.5 g/dl of $(NH_4)_2SO_4$, 1.5 g/dl of $Na_2SO_4$, 0.1 mg/dl of $FeSO_4.7H_2O$, 3.5 μg/l of biotin, 350 μg/l of thiamine hydrochloride and 500 mg/dl of concentrated Stephen's waste by-produced at the steps of the Stephen's method in beet sugar manufacturing factory as the total nitrogen concentration and further 0.01 to 5 g/dl of HETMA, adjusted pH to 6.5, was charged in a 1.0 liter jar fermenter followed by sterilization. Culture was carried out at 31.5° C. under aerial agitation while maintaining the pH between 6.5 and 6.0 with $NH_3$ gas, until the remainting glucose reached 0.5 g/dl.

The yield of L-glutamine based on the weight of sugar is shown in Table 2.

TABLE 2

| Addition Amount of HETMA (g/dl) | Yield of L-Glutamine (%) |
|---|---|
| 0 | 41.0 |
| 0.01 | 41.5 |
| 0.05 | 42.0 |
| 0.25 | 42.5 |
| 0.5 | 43.0 |
| 1.0 | 44.0 |
| 2.0 | 43.0 |
| 3.0 | 41.5 |
| 5.0 | 40.0 |

In the group supplemented with 0.01 to 3 g/dl of HETMA, the yield was more improved than in the control group. From the group supplemented with 1.0 g/dl of HETMA, 1 liter of the culture solution was obtained and cells were removed therefrom by centrifugation. The supernatant was passed through strongly acidic ion exchange resin "DIA ION" SK-1B ($NH_4^+$ type). After washing the resin with water, elution was carried and 35.9 g of L-glutamine crude crystals were obtained from the concentrate.

EXAMPLE 3

A medium containing 13 g/dl of glucose, 6 g/dl of $(NH_4)_2SO_4$, 0.1 g/dl of $KH_2PO_4$, 0.04 g/dl of $MgSO_4.7H_2O$, 1 mg/dl of $FeSO_4.7H_2O$, 1 mg/dl of $MnSO_4.4H_2O$, 100 μg/l of thiamine hydrochloride, 50 g/l of biotin, 500 mg/dl of concentrated Stephen's waste by-produced at the steps of the Stephen's method in beet sugar manufacturing factory as the total nitrogen concentration supplemented with 0.01 to 3.0 g/dl of HETMA and 5 g/dl of calcium carbonate (separately sterilized), was adjusted pH to 7.0 and 20 ml of the medium was charged in a 500 ml flask having a shoulder followed by sterilization with heating.

One platinum loop of Brevibacterium flavum NRRL 12235 was inoculated on the medium and shake cultured for 4 days while keeping at 31.5° C. The yield of L-arginine based on the weight of sugar is shown in Table 3.

TABLE 3

| Addition Amount of HETMA (g/dl) | Yield of L-Arginine (%) |
| --- | --- |
| 0 | 30.5 |
| 0.01 | 31.0 |
| 0.05 | 31.3 |
| 0.25 | 32.0 |
| 0.5 | 33.0 |
| 1.0 | 32.0 |
| 2.0 | 31.0 |
| 3.0 | 29.5 |

From the group supplemented with 0.5 g/dl of HETMA, 1 liter o the culture solution was obtained and cells, etc. were removed therefrom by centrifugation. The supernatant was passed through weakly acidic ion exchange resin "AMBERLITE" C-50 ($NH_4^+$ type). After washing the resin with water, L-arginine was eluted out with $2N-NH_4OH$, the eluate was then concentrated and 30.5 g of L-arginine crude crystals were obtained from the concentrate.

EXAMPLE 4

A medium for producing L-isoleucine was prepared by adding 0.01 to 3 g/dl of DMG to a medium having a composition shown in Table 4 containing glucose as a carbon source. After adjusting the pH to 7.2, 20 ml each was separately charged into each of a shake flask of a 500 ml volume followed by sterilization with heating at 115° C. for 10 minutes.

TABLE 4

| Component | Concentration |
| --- | --- |
| Glucose | 15.0 g/dl |
| $(NH_4)_2SO_4$ | 1.0 g/dl |
| $KH_2PO_4$ | 0.15 g/dl |
| $MgSO_4.7H_2O$ | 0.04 g/dl |
| $FeSO_4.4H_2O$ | 1.0 mg/dl |
| $MnSO_4.4H_2O$ | 1.0 mg/dl |
| Thiamine hydrochloride | 300.0 μg/l |
| Soybean protein acid hydrolysate (T-N) | 25.0 mg/dl |
| Biotin | 5.0 μg/l |
| Stephen's waste (total nitrogen) | 200 mg/dl |
| (Calcium carbonate supplemented after separate sterilization | 5.0 g/dl) |

Brevibacterium flavum FERM-BP 759 obtained by previously culturing was inoculated on each medium and shake cultured at 31.5° C. until glucose disappeared.

The yield of L-isoleucine based on the weight of sugar is shown in Table 5.

TABLE 5

| Addition Amount of DMG (g/dl) | Yield of L-Isoleucine (%) |
| --- | --- |
| 0 | 12.0 |
| 0.01 | 12.5 |
| 0.05 | 12.7 |
| 0.25 | 13.0 |
| 0.5 | 13.3 |
| 1.0 | 13.5 |
| 2.0 | 13.0 |
| 3.0 | 11.5 |

EXAMPLE 5

A medium for producing L-valine was prepared by adding 0.01 to 3 g/dl of TMG of a medium shown in Table 6 containing glucose as a carbon source. After adjusting the pH to 7.0, 20 ml each of the medium was separately charged in each flask of a 500 ml volume followed by sterilization with heating at 115° C. for 10 minutes.

TABLE 6

| Component | Concentration |
| --- | --- |
| Glucose | 15.0 g/dl |
| $(NH_4)_2SO_4$ | 3.0 g/dl |
| $KH_2PO_4$ | 0.1 g/dl |
| $MgSO_4.7H_2O$ | 0.04 g/dl |
| $FeSO_4.4H_2O$ | 1.0 mg/dl |
| $MnSO_4.4H_2O$ | 1.0 mg/dl |
| Thiamine hydrochloride | 30.0 μg/l |
| Soybean protein acid hydrolysate (T-N) | 80.0 mg/dl |
| Biotin | 5.0 μg/l |
| DL-Methionine | 60.0 mg/dl |
| Stephen's waste (total nitrogen) | 200 mg/dl |
| (Calcium carbonate supplemented after separate sterilization | 5.0 g/dl) |

Brevibacterium lactofermentum FERM-P1845 obtained by previously culturing was inoculated on each medium and shake cultured at 31.5° C. until glucose disappeared.

The yield of L-valine based on the weight of sugar is shown in Table 7.

TABLE 7

| Addition Amount of TMG (g/dl) | Yield of L-Valine (%) |
| --- | --- |
| 0 | 12.0 |
| 0.01 | 12.5 |
| 0.05 | 13.0 |
| 0.25 | 13.5 |
| 0.5 | 14.0 |
| 1.0 | 13.5 |
| 2.0 | 12.5 |
| 3.0 | 11.5 |

EXAMPLE 6

In a shake flask of a 500 ml volume 50 ml each of the seed medium having a composition shown in Table 8 was separately charged. After sterilizing by heating at 110° C. for 5 minutes, Brevibacterium flavum ATCC 21475 was inoculated and shake cultured at 31.5° C. for 20 hours to give a seed culture solution. On the other hand, 20 ml each of the medium for producing L-lysine shown in Table 4 was separately charged in a Sakaguchi's flask followed by sterilization. Then 1.5 g of calcium carbonate, which had been previously sterilized by dry heating, was supplemented, respectively and 1 ml each of the above-described seen culture solution was inoculated thereon followed by back-and-forth shake culture at 31.5° C. After 24 hours of the culture, TMG was supplemented in 0, 0.01, 0.05, 0.25, 1.0, 2.0 and 5.0 g/dl per the medium and the culture was continuted. The amount of L-lysine accumulated and the yield are shown in Table 9.

TABLE 8

| Component | Composition of Medium | |
|---|---|---|
| | Seed Medium | Main Fermentation Medium |
| Glucose | 3 g/dl | — |
| Sweet potato molasses | — | 15 g/dl |
| $KH_2PO_4$ | 0.1 g/dl | 0.1 g/dl |
| $MgSO_4.7H_2O$ | 0.04 g/dl | 0.04 g/dl |
| $FeSO_4.7H_2O$ | 1 mg/dl | 1 mg/dl |
| $MnSO_4.4H_2O$ | 1 mg/dl | 1 mg/dl |
| $(NH_4)_2SO_4$ | — | 5.5 g/dl |
| Soybean protein acid hydrolysate (as total nitrogen) | 100 mg/dl | 100 mg/dl |
| Nicotinic amide | 0.5 mg/dl | 1 mg/dl |
| DL-Alanine | 50 mg/dl | 100 mg/dl |
| Biotin | 100 µg/l | 200 µg/l |
| Thiamine hydrochloride | 200 µg/l | 200 µg/l |
| Urea | 0.5 g/dl | — |
| Stephen's waste (total nitrogen) | — | 200 mg/dl |
| pH | 7.0 | 7.0 |

TABLE 9

| Addition Amount of TMG (g/dl) | Amount of L-Lysine Accumulated (g/dl) | Yield of L-Lysine (%) |
|---|---|---|
| 0 | 3.83 | 25.5 |
| 0.01 | 4.10 | 27.3 |
| 0.05 | 4.22 | 28.1 |
| 0.25 | 4.56 | 30.4 |
| 1.0 | 4.35 | 29.0 |
| 2.0 | 4.23 | 28.2 |
| 5.0 | 4.05 | 27.0 |

Fractions which completed the culture in the group supplemented with 0.25 g/dl of TMG were collected and, cells and the calcium salt were removed therefrom by centrifugation. One liter of the supernatant was passed through strongly acidic ion exchange resin ("AMBERLITE" IR-120 CH type) to adsorb L-lysine thereto. Then the absorbed L-lysine was eluted with 3% ammonia water and the eluate was concentrated under reduced pressure.

After hydrochloric acid was added to the concentrate, the system was cooled to precipitate L-lysine as L-lysine hydrochloride dihydrate and give 36.5 g of the crystals.

EXAMPLE 7

A seed medium containing 3 g/dl of glucose, 0.2 g/dl of $(NH_4)_2SO_4$, 0.2 g/dl of urea, 0.15 g/dl of $KH_2PO_4$, 0.04 g/dl of $MgSO_4.7H_2O$, 1 mg/dl of $FeSO_4.7H_2O$, 100 µg/l of thiamine hydrochloride, 300 µ g/l of biotin and 140 mg/dl of soybean protein acid hydrolysate as the total nitrogen, was adjusted pH to 7.0 and 50 ml of the seed medium was charged in a 500 ml flask having a shoulder followed by sterilization with heating. *Brevibacterium flavum* ATCC 21269 and *Escherichia coli* FERM-P 4900 (AJ 11334) were inoculated on the medium, respectively and shake cultured for 12 hours while keeping at 31.5° C. to give a seed culture solution.

On the other hand, 20 ml each of a medium containing 13 g/dl of glucose, 0.25 g/dl of $KH_2PO_4$, 40 mg/dl of $MgSO_47H_2O$, 2.0 g/dl of $(NH_4)_2SO_4$, 1 mg/dl of $MnSO_4.4H_2O$, 1 mg/dl of $FeSO_4.7H_2O$, 40 mg/dl of L-isoleucine, 50 µg/l of biotin, 5 µg/l of thiamine hydrochloride, 32 mg/dl of Stephen's waste as the total nitrogen and a medium further containing 0.01 to 5 g/dl of TMG, adjusted pH to 6.5, was separately charged in a 500 ml flask having a shoulder followed by sterilization with steam at 110° C. for 10 minutes. To each of the medium was added 2 g of calcium carbonate, which had been previously sterilized by dry heating, respectively,, and 1 ml of the above described seed culture solution was further added thereto followed by culturing at 31.5° C. The yield of L-threonine obtained after the culture based on the weight of sugar is shown in Table 10.

TABLE 10

| Addition Amount of TMG (g/dl) | Yield of L-Threonine | |
|---|---|---|
| | *Brevibacterium flavum* (%) | *Escherichia coli* (%) |
| 0 | 12.0 | 25.0 |
| 0.01 | 12.5 | 26.0 |
| 0.05 | 12.8 | 27.5 |
| 0.25 | 13.5 | 28.5 |
| 0.5 | 14.0 | 30.0 |
| 1.0 | 14.5 | 31.0 |
| 2.0 | 13.0 | 28.0 |
| 5.0 | 12.5 | 26.0 |

From the group supplemented with 0.25 g/dl of TMG, 1 liter of the culture solution was obtained and, cells and calcium carbonate were removed from the culture solution by centrifugation. The supernatant, 500 ml, was passed through a column of strongly acidic ion exchange resin ("AMBERLITE" IR-120 (H+ type)). Elution was carried out with 3% ammonia water and the amino acid fractions were collected, desalted, decolored and concentrated under reduced pressure. Alcohol was added to the concentrate. After storing under cooling, the formed crystals were collected and dried to give 7.6 g of threonine crystals having purity of 98% or more.

EXAMPLE 8

To a medium for producing L-histidine shown in Table 11 was added 0.01 to 3 g/dl of MG. After adjusting the pH to 7.2, 20 ml each of the medium was separately charged in a shake flask of a 500 ml volume followed by sterilization with heating at 115° C. for 10 minutes.

TABLE 11

| Component | Concentration |
|---|---|
| Glucose | 13.0 g/dl |
| $(NH_4)_2SO_4$ | 5.0 g/dl |
| $KH_2PO_4$ | 0.1 g/dl |
| $MgSO_4.7H_2O$ | 0.04 g/dl |
| $FeSO_4.4H_2O$ | 1.0 mg/dl |
| $MnSO_4.4H_2O$ | 1.0 mg/dl |
| Thiamine hydrochloride | 50.0 µg/l |

TABLE 11-continued

| Component | Concentration |
| --- | --- |
| Soybean protein acid hydrolysate (T-N) | 30.0 mg/dl |
| Biotin | 50.0 μg/l |
| Stephen's waste (T-N) | 100 mg/dl |
| (Calcium carbonate supplemented after separate sterilization) | 5.0 g/dl |

*Brevibacterium flavum* ATCC 21406 obtained by previously culturing on boillon slant was inoculated on each medium and shake cultured at 31.5° C. until glucose disappeared.

The yield of L-histidine based on the weight of sugar is shown in Table 12.

TABLE 12

| Addition Amount of MG | Yield of L-Histidine |
| --- | --- |
| 0 | 10.0 |
| 0.01 | 10.5 |
| 0.025 | 11.0 |
| 0.5 | 11.5 |
| 1.0 | 12.0 |
| 2.0 | 11.0 |
| 3.0 | 9.5 |

From 1 liter of the culture solution obtained from the group supplemented with 0.5 g/dl of MG, cells and calcium carbonate were removed and the supernatant was passed through strongly acidic ion exchange resin ("AMBERLITE" IR-120 (H+ type)) to adsorbe L-histidine. Thereafter L-histidine adsorbed with 3% ammonia water was eluted and the eluate was then concentrated under reduced pressure. The concentrate was cooled and allowed to stand to precipitate crystals of L-histidine. The crystals were dried to give 7.1 g of L-histidine.

EXAMPLE 9

By adding 0.01 to 3.0 g/dl of DMG to a medium having a composition shown in Table 13 containing sucrose as a carbon source, a medium for producing L-phenylalanine was prepared. After adjusting the pH to 7.0, 20 ml each was separated charged in a shake flask of a 500 ml volume followed by sterilization with heating at 115° C. for 10 minutes.

TABLE 13

| Component | Concentration |
| --- | --- |
| Sucrose | 13.0 g/dl |
| KH$_2$PO$_4$ | 1.5 g/dl |
| (NH$_4$)$_2$SO$_4$ | 1.0 g/dl |
| MgSO$_4$.7H$_2$O | 0.1 g/dl |
| MnSO$_4$.4H$_2$O | 1.0 mg/dl |
| FeSO$_4$.7H$_2$O | 1.0 mg/dl |
| Thiamine hydrochloride | 20.0 μg/l |
| DL-Methionine | 50.0 mg/dl |
| L-Tyrosine | 40.0 mg/dl |
| Soybean protein acid hydrolysate (T-N) | 100.0 mg/dl |
| Fumaric acid | 1.0 g/dl |
| Biotin | 5.0 μg/l |
| Acetic acid | 0.3 ml/dl |
| Glutamic acid | 0.2 g/dl |
| Stephen's waste (T-N) | 100 mg/dl |
| (Calcium carbonate supplemented after separate sterilization) | 5.0 g/dl |

*Brevibacterium lactofermentum* ATCC 21420 obtained by previously culturing on boillon slant was inoculated on each medium and shake cultured at 31.5° C. until glucose disappeared. The yield of L-phenylalanine based on the weight of sugar is shown in Table 14.

TABLE 14

| Addition Amount of DMG (g/dl) | Yield of L-Phenylalanine (%) |
| --- | --- |
| 0 | 9.0 |
| 0.01 | 9.5 |
| 0.02 | 10.5 |
| 0.5 | 11.0 |
| 1.0 | 11.5 |
| 2.0 | 11.0 |
| 3.0 | 10.5 |

EXAMPLE 10

By adding 0.01 to 5 g/dl of TMG to a medium having a composition shown in Table 15 containing glucose as a carbon source, a medium for producing L-tryptophane was prepared. After adjusting the pH to 7.0, 20 ml each was separated charged in a shake flask of a 500 ml volume followed by sterilization with heating at 115° C. for 10 minutes.

TABLE 15

| Component | Concentration |
| --- | --- |
| Glucose | 13.0 g/dl |
| (NH$_4$)$_2$SO$_4$ | 4.0 g/dl |
| KH$_2$PO$_4$ | 0.1 g/dl |
| MgSO$_4$.7H$_2$O | 0.04 g/dl |
| FeSO$_4$.4H$_2$O | 1.0 mg/dl |
| MnSO$_4$.4H$_2$O | 1.0 mg/dl |
| Thiamine hydrochloride | 200 μg/l |
| Casamino acid | 0.1 g/dl |
| Soybean protein acid hydrolysate (T-N) | 30.0 mg/dl |
| L-Phenylalanine | 20.0 mg/dl |
| Biotin | 300.0 μg/l |
| Stephen's waste (T-N) | 100 mg/dl |
| (Calcium carbonate supplemented after separate sterilization) | 5.0 g/dl |

*Bacillus subtilis* FERM-BP 208 obtained by previously culturing was inoculated on each medium and shake cultured at 30° C. until glucose disappeared. The yield of L-tryptophane based on the weight of sugar is shown in Table 16.

TABLE 16

| Addition Amount of TMG (g/dl) | Yield of L-Tryptophane (%) |
| --- | --- |
| 0 | 5.0 |
| 0.01 | 6.0 |
| 0.02 | 6.5 |
| 0.5 | 7.0 |

TABLE 16-continued

| Addition Amount of TMG (g/dl) | Yield of L-Tryptophane (%) |
| --- | --- |
| 1.0 | 7.5 |
| 2.0 | 6.5 |
| 3.0 | 6.0 |
| 5.0 | 5.5 |

EXAMPLE 11

By adding 0.01 to 3 g/dl of DMG to a medium having a composition shown in Table 17 containing glucose as a carbon source, a medium for producing L-serine was prepared. After adjusting the pH to 7.0, 20 ml each was separated charged in a shake flask of a 500 ml volume.

TABLE 17

| Component | Concentration |
| --- | --- |
| Glucose | 13.0 g/dl |
| $(NH_4)_2SO_4$ | 0.2 g/dl |
| $KH_2PO_4$ | 0.2 g/dl |
| $MgSO_4.7H_2O$ | 0.05 g/dl |
| $FeSO_4.4H_2O$ | 2.0 mg/dl |
| Folic acid | 1000 μg/l |
| Thiamine hydrochloride | 1000 μg/l |
| Nicotinic amide | 2500 μg/l |
| Soybean protein acid hydrolysate (T-N) | 60 mg/dl |
| Biotin | 200 μg/l |
| Methionine | 0.1 g/dl |
| L-Leucine | 20 mg/dl |
| Glycine | 3.5 g/dl |
| DL-Methionine | 40 mg/dl |
| Stephen's waste (T-N) | 100 mg/dl |
| (Calcium carbonate supplemented after separate sterilization | 5.0 g/dl) |

*Corynebacterium glycinophilum* FERM-P 1687 obtained by previously culturing was inoculated on each medium and shake cultured at 34° C.

The yield of L-ersine based on the mole of glycine consumed is shown in Table 18.

TABLE 18

| Addition Amount of DMG (g/dl) | Yield of L-Serine (%) |
| --- | --- |
| 0 | 36.0 |
| 0.01 | 37.0 |
| 0.05 | 38.0 |
| 1.0 | 38.5 |
| 2.0 | 37.5 |
| 3.0 | 35.0 |

EXAMPLE 12

To a medium having a composition shown in Table 19 was added 0.1 to 5 g/dl of TMG and 20 ml each of the medium was separately charged in a 500 ml flask having a shoulder followed by sterilization by heating at 120° C. for 10 minutes Cells obtained by culturing *Corynebacterium equi* AJ 11749 (FERM-P 6261) at 31.5° C. for 18 hours in a slant mediumhaving a composition of 20 g/l of glucose, 10 g/l of yeast extract, 10 g/l of peptone, 5 g/l of table salt and 20 g/l of agar (pH 7.2) were inoculated by 3 platinum loops each. After culturing at 34° C. for 2 days, 50 g/l of glucose and 10 g/l of inosine were supplemented followed by shake culture for further 3 days. The amount of 5'-inosinic acid accumulated in the culture solution is shown in Table 20.

TABLE 19

| Component | Concentration |
| --- | --- |
| Glucose | 13 g/dl |
| Yeast extract | 1 g/dl |
| Ammonium sulfate | 0.5 g/dl |
| $KH_2PO_4$ | 2 g/dl |
| $MgSO_4.7H_2O$ | 0.6 g/dl |
| Calcium panthothenate | 1 mg/dl |
| p-Aminobenzoic acid | 1 mg/dl |
| Adenine | 8 mg/dl |
| Biotin | 1000 μg/l |
| Soybean protein acid hydrolysate (T-N) | 90 mg/dl |
| Glutamic acid | 2 μg/l |
| Stephen's waste (T-N) | 100 mg/dl |
| pH | 6.5 |

TABLE 20

| Addition Amount of TMG (g/dl) | Amount 5'-Inosinic Acid Accumulated (5'-IMP.2Na.7.5H$_2$O) |
| --- | --- |
| 0 | 28 |
| 0.1 | 28.5 |
| 0.5 | 29 |
| 1.0 | 30 |
| 2.0 | 29.5 |
| 3.0 | 29 |
| 5.0 | 27 |

EXAMPLE 13

A seed medium containing 3 g/dl of glucose, 0.1 g/dl of $KH_2PO_4$, 0.04 g/dl of $MgSO_4.7H_2O$, 0.001 g/dl of $FeSO_4.7H_2O$, 0.001 g/dl of $MnSO_4.4H_2O$, 0.3 g/dl of urea, soybean protein acid hydrolysate containing 60 mg/dl as the total nitrogen, 30 μg/dl of thiamine hydrochloride and 20 μg/l of biotin was adjusted pH to 6.0 and 50 ml of the seed medium was charged in a 500 ml flask having a shoulder followed by sterilization with heating.

*Brevibacterium lactofermentum* FERM-P 5936 (AJ 11678) was inoculated on the medium and shake cultured for 13 hours while keeping at 31.5° C.

On the other hand, 20 ml each of a medium containing 13 g/dl of glucose, 0.1 g/dl of $KH_2PO_4$, 0.04 g/dl of $MgSO_4. 7H_2O$, 0.001 g/dl of $FeSO_4.7H_2O$, 0.001 g/dl of $MnSO_4.4H_2O$, 4.0 g/dl of ammonium sulfate, 65 mg/dl of soybean protein acid hydrolysate as the total nitrogen, 20 μg/dl of thiamine hydrochloride, 10 μg/dl of biotin and 70 mg/dl of L-arginine and a medium further containing 0.01 to 3 g/dl of DMG, adjusted pH to 7.0, respectively followed by sterilization with heating at 115° C. for 10 minutes. To each medium 2 g of calcium carbonate, which had been previously sterilized by dry heating, was added, respectively and, 1 ml each of the above-described seed culture solution was added thereto followed by culturing at 31.5° C. The yield of L-ornithine after completion of the culture based on sugar is shown in Table 21.

TABLE 21

| Addition Amount of DMG (g/dl) | Yield of L-Ornithine (%) |
|---|---|
| 0 | 24.5 |
| 0.01 | 26.0 |
| 0.05 | 27.5 |
| 1.0 | 29.0 |
| 2.0 | 27.0 |
| 3.0 | 23.0 |

EXAMPLE 14

A seed medium containing 3 g/dl of glucose, 0.1 g/dl of $KH_2PO_4$, 0.04 g/dl of $MgSo_4\ 7H_2O$, 0.001 g/dl of $FeSO_4.7H_2O$, 0.001 g/dl of $MnSO_4.4H_2O$, 0.3 g/dl of urea, 60 mg/dl of soybean protein acid hydrolysate as the total nitrogen, 30 μg/l of thiamine hydrochloride and 20 μg/l of biotin was adjusted pH to 6.0 and 50 ml of the seed medium was charged in a 500 ml flask having a shoulder followed by sterilization with heating.

Corynebacterium glutamicum ATCC 13232 was inoculated on the medium and shake cultured for 13 hours while keeping at 31.5° C.

On the other hand, 20 ml each of a medium containing 13 g/dl of glucose, 0.1 g/dl of $KH_2PO_4$, 0.04 g/dl of $MgSO_4.7H_2O$, 0.001 g/dl of $MnSO_4.4H_2O$, 4.0 g/dl of ammonium sulfate, 65 mg/dl of soybean protein acid hydrolysate as the total nitrogen, 20 μg/l of thiamine hydrochloride, 10 μg/dl of biotin and 70 mg/dl of L-homoserine and a medium further containing 0.01 to 3 g/dl of DMG, adjusted pH to 7.0, was separately charged in a 500 ml flask having a shoulder followed by sterilization with heating at 115° C. for 10 minutes. To each of the medium was added 2 g of calcium carbonate which had been previously sterilized by dry heating and, 1 ml each of the above-described seed culture solution was added thereto followed by culturing at 31.5° C. The yield of L-ornithine after completion of the culture based on sugar is shown in Table 22.

TABLE 22

| Addition Amount of DMG (g/dl) | Yield of L-Ornithine (%) |
|---|---|
| 0 | 24.5 |
| 0.01 | 26.0 |
| 0.05 | 27.5 |
| 1.0 | 29.0 |
| 2.0 | 27.0 |
| 3.0 | 23.0 |

EXAMPLE 15

A seed medium containing 3 g/dl of glucose, 0.1 g/dl of $KH_2PO_4$, 0.04 g/dl of $MgSO_4.7H_2O$, 1.0 mg/dl of $FeSO_4.7H_2O$, 1.0 mg/dl of $MnSO_4.4H_2O$, 0.3 g/dl of urea, 60 mg/dl of soybean protein acid hydrolysate as the total nitrogen, 30 γ/dl of thiamine hydrochloride and b 20 61 γ/dl of biotin, was adjusted pH to 6.0 and 50 ml of the seed medium was charged in a 500 ml flask having a shoulder followed by sterilization with heating. Corynebacterium glutamicum FERM-P 5643 (AJ 11588) was inoculated on the medium and shake cultured for 13 hours while keeping at 31.5° C.

On the other hand, culture was carried out in a manner similar to Example 14 with respect to each of a medium containing 13 g/dl of glucose, 0.1 g/dl of $KH_2PO_4$, 0.04 g/dl of $MgSO_4.7H_2O$, 1.0 mg/dl of $FeSO_4.7H_2O$, 1.0 mg/dl of $MnSO_4.\ 4H_2O$, 3.0 g/dl of ammonium chloride, 65 mg/dl of soybean protein acid hydrolysate as the toal nitrogen, 20 γ/dl of thiamine hydrochloride, 10 γ/dl of biotin and 70 mg/dl of L-arginine and a medium further containing 0.01 to 3 g/dl of MG, adjusted pH to 7.0. The yield of L-citrulline based on sugar after completion of the culture is shown in Table 23.

TABLE 23

| Addition Amount of MG (g/dl) | Yield of L-Citrulline (%) |
|---|---|
| 0 | 13.5 |
| 0.01 | 14.0 |
| 0.05 | 14.5 |
| 1.0 | 15.5 |
| 2.0 | 14.0 |
| 3.0 | 13.0 |

EXAMPLE 16

A seed medium having a composition shown in Table 24 was separately charged in a shake flask of a 500 ml volume by 50 ml each. After sterilization by heating at 110° C. for 5 minutes, Corynebacterium glutamicum FERM-P 5836 (AJ 11655) was inoculated ans shake cultured at 31.5° C. for 12 hours to give a seed culture solution.

On the other hand, culture was carried out in a manner similar to Example 14 with respect to each of a L-tryosine main fermentation medium shown in Table 24 and a medium further containing 0.01 to 3 g/dl of HETMA. The amount of L-tyrosine after completion of the culture is shown in Table 25.

TABLE 24

| Component | Composition of Medium | |
|---|---|---|
| | Seed Medium | Main Fermentation Medium |
| Glucose | 3 g/dl | 13 g/dl |
| Urea | 0.3 g/dl | — |
| Ammonium acetate | 0.5 g/dl | 1.0 g/dl |
| Ammonium sulfate | — | 3.0 g/dl |
| $KH_2PO_4$ | 0.1 g/dl | 0.2 g/dl |
| $MgSO_4.7H_2O$ | 0.04 g/dl | 0.1 g/dl |
| $MnSO_4.4H_2O$ | 1 mg/dl | 1 mg/dl |
| $FeSO_4.7H_2O$ | 1 mg/dl | 1 mg/dl |
| Thiamine hydrochloride | 300 μg/l | 50 μg/l |
| Biotin | 200 μg/l | 100 μg/l |
| DL-Phenylalanine | — | 50 mg/dl |
| Defatted soybean protein acid hydrolysate (as total nitrogen) | 6.5 ml/l | — |
| pH | 7.0 | 7.0 |

TABLE 25

| Addition Amount of HETMA (g/dl) | Yield of L-Tyrosine (%) |
|---|---|
| 0 | 6.0 |
| 0.01 | 6.5 |
| 0.03 | 8.0 |
| 0.5 | 9.0 |
| 1.0 | 8.2 |
| 2.0 | 7.5 |
| 3.0 | 6.0 |

EXAMPLE 17

A seed medium containing 3 g/dl of glucose, 0.1 g/dl of $KH_2PO_4$, 0.3 g/dl of urea, 0.04 g/dl of $MgSO_4.7H_2O$, 1 mg/dl of $FeSO_4.7H_2O$, 1 mg/dl of $MnSO_4.4H_2O$, 40 mg/dl of DL-methionine, 10 μg/l of biotin, 200 ∝g/l of thiamine hydrochloride and 50 mg/dl of soybean protein acid hydrolysate as the total nitrogen, was adjusted pH to 6 and 50 ml of the seed medium was charged in a 500 ml flask having a shoulder followed by sterilization with heating at 120° C. for 10 minutes. *Brevibacterium flavum* FERM-BP 755 was inoculated on the medium and shake cultured for 20 hours while keeping at 31.5° C.

On the other hand, culture was carried out in a manner similar to Example 14 with respect to each of a medium containing 13 g/dl of beet molasses (calculated as glucose) 0.1 g/dl of $KH_2PO_4$, 2.0 g/dl of $(NH_4)_2SO_4$, 0.04 g/dl of $MgSO_4 0.7H_2O$, 1 mg/dl of $FeSO_4.7H_2O$, 1 mg/dl of $MnSO_4.4H_2O$, 100 mg/dl of DL-methionine, 50 μg/l of biotin and 300 μg/l of thiamine hydrochloride and 50 mg/dl of defatted soybean protein acid hydrolysate and a medium further containing 0.01 to 3 g/dl of HETMA, adjusted to pH 7.0. The amount of L-leucine produced after completion of the culture is shown in Table 26.

TABLE 26

| Addition Amount of HETMA (g/dl) | Yield of L-Leucine (%) |
|---|---|
| 0 | 12.0 |
| 0.01 | 13.2 |
| 0.5 | 14.2 |
| 1.0 | 15.0 |
| 2.0 | 14.0 |

TABLE 26-continued

| Addition Amount of HETMA (g/dl) | Yield of L-Leucine (%) |
|---|---|
| 3.0 | 12.5 |

What is claimed is:

1. A process for producing 5'-inosinic acid, which comprises culturing 5'-inosinic acid-producing bacteria in a medium containing inosine, and can molasses, sucrose or glucose as a main carbon source and containing at least one substance selected from the group consisting of L-methylglycine, N,N-dimethylglycine, N,N,N-trimethylglycine and (2-hydroxyethyl)trimethylammonium in an amount effective to enhance the yield of 5'-inosinic acid; and harvesting said 5'-inosinic acid.

2. The process according to claim 1, wherein said at least one substance is incorporated in said medium in a concentration of about 0.01-5%.

3. The process according to claim 1, wherein said at least one substance in incorporated in said medium in a concentration of about 0.05-2.0%.

4. The process according to claim 1, wherein said medium further contains as a carbon source one or more compounds selected from the group consisting of fructose, maltose, sweet potato molasses, sweet potato blackstrap molasses, beet molasses, beet blackstrap molasses, crude sugar, saccharified starch liquid, saccharified cellulose liquid, saccharified pulp liquid, lactose, acetic acid, propionic acid, benzoice acid, pyruvic acid, citric acid, succinic acid, fumaric acid, malic acid, ethyl alcohol and butyl alcohol.

5. The process according to claim 1, wherein said medium further contains a nitrogen source and inorganic salts.

6. The process according to claim 1, wherein said 5'-inosinic acid-producing bacteria are cultured at a temperature in the range of about 20° to 40° C. at a pH which is substantially neutral.

* * * * *

UNITED STATES PATENT AND TRADEMARK OFFICE
CERTIFICATE OF CORRECTION

PATENT NO.  :  5,164,306

DATED       :  NOVEMBER 17, 1992

INVENTOR(S) :  YASHUHIKO YOSHIHARA ET AL

It is certified that error appears in the above-identified patent and that said Letters Patent is hereby corrected as shown below:

Column 2, line 64, "FERM-P 6517" should read --FERM-P 5417--.

Column 3, line 60, "FERM0P" should read --FERM-P--.

Column 5, line 48, "Dur.ing" should read --During--;
    line 55, after "sugar" insert --consumed was substantially reduced, the supply of the sugar--.

Column 6, line 17, "portein" should read --protein--;
    line 61, after "carried" insert --out with $2N-NH_4OH$, the eluate was then concentrated--.

Column 7, line 9, "Brevibacterium flavum" should read in italics --*Brevibacterium flavum*--;
    line 29, "liter o" should read --liter of--.

Column 9, line 7, "seen" should read --seed--;
    lines 11 and 12, "continuted" should read --continued--.

UNITED STATES PATENT AND TRADEMARK OFFICE
CERTIFICATE OF CORRECTION

PATENT NO. : 5,164,306

DATED : NOVEMBER 17, 1992

INVENTOR(S) : YASHUHIKO YOSHIHARA ET AL

It is certified that error appears in the above-identified patent and that said Letters Patent is hereby corrected as shown below:

Column 10, line 20, "above described" should read --above-described--.

Column 11, line 35, "absorbe" should read --absorb--.

Column 13, line 44, "L-ersine" should read --L-serine--;
line 65, "mediumhaving" should read --medium having--.

Column 15, line 23, "Corynebacterium glutamicum" should read in italics --*Corynebacterium glutamicum*--;
line 60, "b 20 61 γ/dl" should read --20 γ/dl--.

Column 16, line 28, "ans" should read --and--;
line 33, "L-tryosine" should read --L-tyrosine--.

Column 17, line 22, "$MgSO_40.7H_2O$", should read --$MgSO_4.7H_2O$--.

Column 18, line 12, Claim 1, "can" should read --cane--;
line 32, Claim 4, "benzoice" should read --benzoic--.

Signed and Sealed this

Third Day of May, 1994

Attest:

BRUCE LEHMAN

Attesting Officer    Commissioner of Patents and Trademarks